United States Patent [19]

Berg et al.

[11] Patent Number: 4,549,938
[45] Date of Patent: Oct. 29, 1985

[54] SEPARATION OF METHANOL FROM METHYL ACETATE BY EXTRACTIVE DISTILLATION

[76] Inventors: Lloyd Berg; An-I Yeh, both of 1314 S. Third Ave., Bonzeman, Mont. 59715

[21] Appl. No.: 592,600

[22] Filed: Mar. 23, 1984

Related U.S. Application Data

[62] Division of Ser. No. 485,006, Apr. 14, 1983.

[51] Int. Cl.⁴ .......................... B01D 3/40; C07C 29/84
[52] U.S. Cl. ........................................ 203/51; 203/56; 203/57; 203/58; 203/64; 568/913
[58] Field of Search .................. 560/248; 568/913; 203/58, 51, 56, 57, 64, 65

[56] References Cited

U.S. PATENT DOCUMENTS

| 2,325,379 | 7/1943 | Durrum | 203/57 |
| 2,623,845 | 12/1952 | Coutor | 203/51 |
| 3,190,813 | 6/1965 | Vogt et al. | 203/57 |
| 3,268,572 | 8/1966 | Knörr et al. | 203/60 |
| 3,431,181 | 3/1969 | Bouniot | 203/60 |
| 4,431,838 | 2/1984 | Feldman et al. | 560/248 |

FOREIGN PATENT DOCUMENTS

| 234662 | 12/1963 | Austria | 203/58 |
| 1088040 | 9/1960 | Fed. Rep. of Germany | 203/64 |
| 1089744 | 9/1960 | Fed. Rep. of Germany | 203/64 |
| 119411 | 9/1979 | Japan | 203/64 |
| 967471 | 8/1964 | United Kingdom | 203/60 |
| 642295 | 1/1979 | U.S.S.R. | 203/56 |

Primary Examiner—Wilbur Bascomb

[57] ABSTRACT

Methanol cannot be completely removed from methanol-methyl acetate mixtures by distillation because of the presence of the minimum binary azeotrope. Methanol can be readily removed from mixtures containing it and methyl acetate by using extractive distillation in which the extractive distillation agent is a higher boiling oxygenated or nitrogenous organic compound or a mixture of these. Typical examples of effective agents are: ethylene glycol phenyl ether, ethylene carbonate, nitromethane, 2-nitrotoluene, 1-nitropropane plus propylene carbonate.

23 Claims, No Drawings

SEPARATION OF METHANOL FROM METHYL ACETATE BY EXTRACTIVE DISTILLATION

This application is a divisonal of application Ser. No. 485,006 filed Apr. 14, 1983.

FIELD OF THE INVENTION

This invention relates to a method for separating methanol from methyl acetate using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continously removed from the column. The usual methods of separation of these two components are the use of another rectification column, cooling and phase separation, or solvent extraction.

One of the commercially important ways to manufacture methyl acetate is by the catalytic esterification of methanol with acetic acid. Methyl acetate, (b.p.=56.3° C.) and methanol (b.p.=64.5° C.) form a binary azeotrope boiling at 54° C. and conatining 81.3 weight percent methyl acetate, 18.7 weight percent methanol. Methyl acetate also forms a binary azeotrope with water which boils at 56.1° C. and contains 95 weight percent methyl acetate. Methyl acetate, methanol and water do not form a ternary azeotrope. Thus in the esterification of methanol with acetic acid to form methyl acetate and water, the rectification of this mixture yields the lowest boiling constituent, namely the methyl acetate-methanol azeotrope. It is therefore impossible to produce methanol from methyl acetate mixtures by rectification because of the lower boiling azeotrope will always come off overhead as the initial product. Any mixture of methanol and methyl acetate subjected to rectification at one atmosphere pressure will produce an overhead product boiling at 54.0° C. and containing 81.3 wt. % methyl acetate, 18.7 wt. % methanol. Extractive distillation would be an attractive method of effecting the separation of methanol from methyl acetate if agents can be found that (1) will break the methanol-methyl acetate azeotrope and (2) are easy to recover from the methyl acetate, that is, form no azeotrope with methyl acetate to make the separation by rectification possible with only a few theoretical plates.

Extractive distillation typically requires the addition of an equal amount to twice as much extractive agent as the methanol-methyl acetate on each plate in the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with methyl acetate otherwise it will form a two phase azeotrope with the methyl acetate in the revovery column and some other method of separation will have to be employed.

The breaking of this azeotrope by extractive distillation is a new concept. The closest application of the concept might be the breaking of the ethanol-water azeotrope. J. Schneible, (U.S. Pat. No. 1,469,447) used glycerol; P. V. Smith & C. S. Carlson, (U.S. Pat. No. 2,559,519) employed ethoxyethanol and butoxyethanol for this purpose and W. E. Catterall (U.S. Pat. No. 2,591,672) reported gasoline as being effective. These are dehydrations and operate more conventionally as a solvent extraction process rather than an extractive distillation.

OBJECTIVE OF THE INVENTION

The object of this invention is to provide a process or method of extractive distillation that will enhance the relative volatility of methanol from methyl acetate in their separation in a rectification column. It is a further object of this invention to identify suitable extractive distillation agents which will eliminate the methanol-methyl acetate binary azeotrope and make possible the production of pure methanol and methyl acetate by rectification. It is a further object of this invention to identify organic compounds which, in addition to the above constraints, are stable, can be separated from methyl acetate by rectification with relatively few theoretical plates and can be recycled to the extractive distillation column and re-used with little decomposition.

SUMMARY OF THE INVENTION

The objects of this invention are provided by a process for separating methanol from methyl acetate which entails the use of certain oxygenated and nitrogenous organic compounds as the agent in extractive distillation.

DETAILED DESCRIPTION OF THE INVENTION

We have discovered that certain oxygenated and nitrogenous organic compounds, some individually but principally as mixtures, will effectively negate the methanol-methyl acetate azeotrope and permit the separation of pure methanol from methyl acetate by rectification when employed as the agent in extractive distillation. Table 1 lists the compounds, mixtures and approximate proportions that we have found to be effective. The data in Table 1 was obtained in a vapor-liquid equilibrium still. In each case, the starting material was the methanol-methyl acetate azeotrope. The ratios are the parts by weight of extractive agent used per part of methanol-methyl acetate azeotrope. The relative volatilities are listed for each of the two ratios employed.

The compounds that are effective as extractive distillation agents when used alone are ethylene carbonate, propylene carbonate, ethylene glycol phenyl ether, nitromethane, nitroethane, 1-nitropropane, 2-nitropropane, nitrobenzene, 2-nitrotoluene, 3-nitrotoluene, 4-nitrotoluene, 2-nitro-m-xylene, 3-nitro - o-xylene and 4-nitro - o-xylene. The compounds which are effective when used in mixtures of two or more components are all of the above and dimethylsulfoxide.

The two relative volatilities shown in Table 1 correspond to the two different ratios employed. For example in Table 1, one part of nitrobenzene with one part of methanol-methyl acetate azeotrope gives a relative volatility of 2.40, 6/5 parts of nitrobenzene gives 3.30. One half part of 1-nitropropane mixed with one half part of propylene carbonate with one part of methanol-methyl acetate azeotrope gives a relative volatility of 1.92, 3/5 parts of 1-nitropropane plus 3/5 parts of propylene carbonate gives 2.00.

TABLE 1

Extractive Distillation Agents Which Are Effective In Separating Methanol From Methyl Acetate

| Compounds | Ratios | | Relative Volatilities | |
|---|---|---|---|---|
| Ethylene carbonate | 2 | | 1.06 | |
| Propylene carbonate | " | 12/5 | 1.06 | 1.52 |
| Ethylene glycol phenyl ether | " | " | 1.03 | 1.28 |
| Nitromethane | " | | 2.08 | |
| Nitroethane | " | | 2.40 | |
| 1-Nitropropane | " | | 2.65 | |
| 2-Nitropropane | " | | 2.77 | |
| Nitrobenzene | " | " | 2.40 | 3.30 |
| 2-Nitrotoluene | " | " | 2.08 | 2.27 |
| 3-Nitrotoluene | " | | 2.22 | |
| 4-Nitrotoluene | " | " | 2.38 | 2.08 |
| 2-Nitro-m-xylene | " | | 1.54 | |
| 3-Nitro-o-xylene | " | | 1.67 | |
| 4-Nitro-o-xylene | " | | 1.89 | |
| Propylene carbonate, Ethylene glycol phenyl ether | 1:1 | 6/5:6/5 | 1.10 | 1.07 |
| Nitromethane, Ethylene carbonate | " | " | 1.75 | 1.45 |
| Nitromethane, Propylene carbonate | " | " | 1.70 | 1.64 |
| Nitroethane, Ethylene carbonate | " | " | 1.64 | 1.78 |
| Nitroethane, Propylene carbonate | " | " | 1.85 | 1.85 |
| 1-Nitropropane, Ethylene carbonate | " | " | 1.66 | 1.54 |
| 1-Nitropropane, Propylene carbonate | " | " | 1.92 | 2.00 |
| 2-Nitropropane, Ethylene carbonate | " | " | 1.82 | 1.66 |
| 2-Nitropropane, Propylene carbonate | " | " | 1.64 | 1.79 |
| Nitrobenzene, Ethylene carbonate | " | " | 1.56 | 1.37 |
| Nitrobenzene, Propylene carbonate | " | " | 1.64 | 1.59 |
| Nitrobenzene, Ethylene glycol phenyl ether | " | " | 1.19 | 1.30 |
| 2-Nitrotoluene, Propylene carbonate | " | " | 1.64 | 2.04 |
| 3-Nitrotoluene, Propylene carbonate | " | " | 1.75 | 1.96 |
| 3-Nitrotoluene, Ethylene glycol phenyl ether | " | " | 1.15 | 1.37 |
| 4-Nitrotoluene, Propylene carbonate | " | " | 1.89 | 2.22 |
| 2-Nitrotoluene, Ethylene glycol phenyl ether | " | " | 1.07 | 1.38 |
| 2-Nitro-m-xylene, Propylene carbonate | " | | 1.37 | |
| 2-Nitro m-xylene, Ethylene carbonate | " | | 1.38 | |
| 3-Nitro o-xylene, Propylene carbonate | " | | 1.30 | |
| 3-Nitro o-xylene, Ethylene carbonate | " | | 1.37 | |
| 4-Nitro o-xylene, Propylene carbonate | " | | 1.50 | |
| 4-Nitro o-xylene, Ethylene carbonate | " | | 1.50 | |
| Ethylene carbonate, propylene carbonate, ethylene glycol phenyl ether | $(\frac{2}{3})^3$ | $(4/5)^3$ | 1.07 | 1.11 |
| Nitromethane, Ethylene carbonate, Et glycol ∅ ether | " | " | 1.31 | 1.39 |
| Nitromethane, Propylene carbonate, Et glycol ∅ ether | " | " | 1.45 | 1.23 |
| Nitroethane, Ethylene carbonate, Dimethylsulfoxide | " | " | 1.41 | 1.31 |
| Nitroethane, Propylene carbonate, Et glycol ∅ ether | " | " | 1.47 | 1.58 |
| 1-Nitropropane, Ethylene carbonate, Et glycol ∅ ether | " | " | 1.23 | 1.61 |
| 1-Nitropropane, Propylene carbonate, Et glycol ∅ ether | " | " | 1.43 | 1.49 |
| 2-Nitropropane, Ethylene carbonate, Et glycol ∅ ether | " | " | 1.44 | 1.43 |
| 2-Nitropropane, Propylene carbonate, Et glycol ∅ ether | " | " | 1.58 | 1.70 |
| Nitrobenzene, Ethylene carbonate, Et glycol ∅ ether | " | " | 1.25 | 1.33 |
| Nitrobenzene, Propylene carbonate, Et glycol ∅ ether | " | " | 1.49 | 1.54 |
| 2-Nitrotoluene, Ethylene carbonate, Et glycol ∅ ether | " | " | 1.16 | 1.39 |
| 2-Nitrotoluene, Propylene carbonate, Et glycol ∅ ether | " | " | 1.45 | 1.51 |
| 3-Nitrotoluene, Ethylene carbonate, Et glycol ∅ ether | " | " | 1.28 | 1.49 |
| 3-Nitrotoluene, Propylene carbonate, Et glycol ∅ ether | " | " | 1.42 | 1.33 |
| 4-Nitrotoluene, Propylene carbonate, Et glycol ∅ ether | " | | 1.43 | |
| 4-Nitrotoluene, Ethylene carbonate, Et glycol ∅ ether | " | | 1.27 | |
| 2--Nitro m-xylene, Propylene carbonate, Et glycol ∅ ether | " | | 1.23 | |
| 2-Nitro m-xylene, Ethylene carbonate, Et glycol ∅ ether | " | | 1.20 | |
| 3-Nitro o-xylene, Propylene carbonate, Et glycol ∅ ether | " | | 1.39 | |

TABLE 1-continued

Extractive Distillation Agents Which Are Effective In
Separating Methanol From Methyl Acetate

| Compounds | Ratios | Relative Volatilities |
|---|---|---|
| 3-Nitro o-xylene, Ethylene carbonate, Et glycol ∅ ether | " | 1.20 |
| 2-Nitrotoluene, 2-Nitropropane, Propylene carbonate | " | 1.39 |
| 4-Nitro o-xylene, Propylene carbonate, Et glycol ∅ ether | " | 1.20 |
| 4-Nitro o-xylene, Ethylene carbonate, Et glycol ∅ ether | " | 1.19 |

TABLE 2

Data From Runs Made In Rectification Column

| Compounds | Temp., °C. Overhead | Wt. % Methanol Overhead | Wt. % Methanol Bottoms | Relative Volatility |
|---|---|---|---|---|
| Nitromethane | 62.2 | 75.3 | 10.6 | 2.06 |
| Nitroethane | 61.8 | 77.9 | 6.4 | 2.40 |
| 1-Nitropropane | 60.8 | 74.0 | 3.4 | 2.65 |
| 2-Nitropropane | 61.8 | 78.9 | 3.7 | 2.77 |
| Nitrobenzene | 60.6 | 76.5 | 11.0 | 2.08 |
| Nitrobenzene (R) | 60.0 | 77.2 | 12.3 | 2.04 |
| Propylene carbonate + 1-Nitropropane (R) | 55.4 | 36.1 | 7.2 | 1.55 |

Notes:
Feed mixture was 75 grams Methanol + 425 grams Methyl acetate Agents were added at a rate of 20 ml/min & 48° C.
R indicates agent was reclaimed and re-used Compositions are calculated on agent-free basis One third parts of 2-nitrotoluene plus ⅓ parts of propylene carbonate plus ⅓ parts of ethylene glycol phenyl ether mixed with one part of methanol-methyl acetate azeotrope gives a relative volatility of 1.45, with 2/5 parts, these three give 1.51. In every example in Table 1, the starting material is the methanol-methyl acetate azeotrope which possesses a relative volatility of 1.00. Several of the compounds and mixtures listed in Table 1 and whose relative volatility has been determined in the vapor-liquid equilibrium still, were then evaluated in a glass perforated plate rectification column possessing 4.5 theoretical plates. The results are listed in Table 2. The methanol-methyl acetate mixture studied contained 85 wt. % methyl acetate, 15 wt. % methanol. The methanol-methyl acetate azeotrope contains 81.3 wt. % methyl acetate, 18.7 wt. % methanol. In every case the feed or bottoms composition contained less than 18.7% methanol and in every case the overhead is richer than 18.7% methanol. Without the extractive agent, the overhead would be the azeotrope, 18.7% methanol. This proves that the extractive agent is negating the azeotrope and makes the rectification proceed as if the azeotrope no longer existed and brings methanol out as overhead. It is our belief that this is the first time that this has been accomplished. We are bringing methanol, normally the less volatile component, out as overhead and the more volatile component, methyl acetate, comes out in the bottoms or stillpot with the extractive distillation agent.

The data in Table 2 was obtained in the following manner. The data is for the extractive distillation agents designated. Here we have negated the azeotrope. The temperature of the overhead approaches 63° C., the boiling point of pure methanol at 630 mm. Hg. and the methyl acetate goes to the stillpot with the extractive distillation agent. The designation "R" by the extractive distillation agent means that the same material was recovered and re-used to show its stability in repeated operation. When the methanol-extractive distillation agent mixture taken from the stillpot is redistilled, methyl acetate comes off overhead in the usual way at its normal boiling point, 52° C. at 630 mm. Hg.

THE USEFULNESS OF THE INVENTION

The usefulness or utility of this invention can be demonstrated by referring to the data presented in Tables 1 and 2. All of the successful extractive distillation agents show that methanol and methyl acetate can be separated from their binary azeotrope by means of distillation in a rectification column and that the ease of separation as measured by relative volatility is considerable. Without these extractive agents, no improvement in the weight percent of methanol above the azeotrope composition will occur in the recification column. The data also show that the most attractive agents will operate at a boilup rate low enough to make this a useful and efficent method of recovering high purity methanol from any mixture of these two including the binary minimum azeotrope. The stability of the compounds used and the boiling point difference is such that complete recovery and recycle is obtainable by a simple distillation and the amount required for make-up is small.

WORKING EXAMPLES

Example 1

The methanol-methyl acetate azeotrope is 81.3 wt. % methyl acetate, 18.7 wt. % methanol. Fifty grams of the methanol-methyl acetate azeotrope and fifty grams of 4-nitrotoluene were charged to an Othmer type glass vapor-liquid equilibrium still and refluxed for eleven hours. Analysis of the vapor and liquid by gas chromatography gave vapor 80.3% methyl acetate, 19.7% methanol; liquid of 90.7% methyl acetate, 9.3% methanol. This indicates a relative volatility of 2.38. Ten grams of 4-nitrotoluene were added and refluxing continued for another 12 hours. Analysis indicated a vapor composition of 80% methyl acetate, 20% methanol, a liquid composition of 89.3% methyl acetate, 10.7% methanol which is a relative volatilty of 2.08.

Example 2

Fifty grams of the methanol-methyl acetate azeotrope, 25 grams of 1-nitropropane and 25 grams of propylene carbonate were charged to the vapor-liquid equilibrium still and refluxed for 11 hours. Analysis indicated a vapor composition of 82% methyl acetate, 18% methanol, a liquid composition of 89.7% methyl acetate, 10.3% methanol which is a relative volatility of 1.92. Five grams of 1-nitropropane and five grams of propylene carbonate were added and refluxing continued for another 12 hours. Analysis indicated a vapor composition of 82.5% methyl acetate, 17.5% methanol, a liquid composition of 90.5% methyl acetate, 9.5% methanol which is a relative volatility of 2.00.

Example 3

Fifty grams of the methanol-methyl acetate azeotrope, 17 grams of 2-nitropropane, 17 grams of propylene carbonate and 17 grams of ethylene glycol phenyl ether were charged to the vapor-liquid equilibrium still and refluxed for 15 hours. Analysis indicated a vapor composition of 83.3% methyl acetate, 16.7% methanol, a liquid composition of 88.8% methyl acetate, 11.2% methanol which is a relative volatility of 1.58. Three grams each of 2-nitropropane, propylene carbonate and ethylene glycol phenyl ether were added and refluxing continued for another nine hours. Analysis indicated a vapor composition of 84.7% methyl acetate, 15.3% methanol, a liquid composition of 90.3% methyl acetate, 9.7% methanol which is a relative volatility of 1.70.

Example 4

A glass perforated plate rectification column was calibrated with ethylbenzene and p-xylene which mixture possesses a relative volatility of 1.06 and found to have 4.5 theoretical plates. A solution of 75 grams of methanol and 425 grams of methyl acetate was placed in the stillpot and heated. When refluxing began, an extractive agent consisting of pure 2-nitropropane was pumped into the column at a rate of 20 ml/min. The temperature of the extractive agent as it entered the column was 48° C. After establishing the feed rate of the extractive agent, the heat input to the methanol and methyl acetate in the stillpot was adjusted to give a total reflux rate of 10-20 ml/min. After one hour of operation, the overhead and bottoms samples of approximately two ml. were collected and analysed using gas chromatography. The overhead analysis was 75.5% methanol, 24.5% methyl acetate. The bottoms analysis was 5.5% methanol, 94.5% methyl acetate. Using these compositions in the Fenske equation, with the number of theoretical plates in the column being 4.5, gave an average relative volatility of 2.42 for each theoretical plate. After 1.5 hours of total operating time, the overhead and bottoms samples were again taken and analysed. The overhead composition was 78.9% methanol, 21.1% methyl acetate and the bottoms composition was 3.7% methanol, 96.3% methyl acetate. This gave an average relative volatility of 2.77 for each theoretical plate. After two hours of total operating time, the overhead and bottoms samples were again taken and analysed. The overhead composition was 81.8% methanol, 18.2% methyl acetate and the bottoms composition was 4% methanol, 96% methyl acetate. This gave an average relative volatility of 2.83 for each theoretical plate.

Example 5

A solution of 75 grams of methanol and 425 grams of methyl acetate was placed in the stillpot of the same column used in example 4 and heat applied. When the refluxing began, an extractive agent of 50% 1-nitropropane and 50% propylene carbonate was feed into the top of the column at a feed rate of 20 ml/min. and a temperature of 48° C. After establishing the feed rate of the extractive agent, the heat input to the methanol and methyl acetate in the stillpot was adjusted to give a total reflux of 10-20 ml/min. Having established the reflux rate, the column was allowed to operate for one hour. After one hour of steady operation, overhead and bottoms samples of approximately two ml. were collected and analysed using gas chromatography. The overhead analysis was 34.5% methanol, 65.4% methyl acetate, the bottoms analysis was 7.8% methanol, 92.2% methyl acetate. Using these compositions in the Fenske equation with the number of theoretical plates in the column being 4.5, gave an average relative volatility of 1.50 for each theoretical plate. After 1.5 hours of total operating time, the overhead composition was 36.1% methanol, 63.9% methyl acetate and the bottoms composition was 7.2% methanol, 92.8% methyl acetate. This gave an average relative volatility of 1.55 for each theoretical plate. After two hours of total operating time, the overhead composition was 35% methanol, 65% methyl acetate and the bottoms composition was 6.7% methanol, 93.3% methyl acetate. This gave an average relative volatility of 1.56 for each theoretical plate.

The nature of the present invention having been described, what we wish to claim as new and useful and secure by Letters Patent is:

1. A method for recovering methanol from a mixture of methanol and methyl acetate which comprises distilling a mixture of methanol and methyl acetate in a rectification column in the presence of about one to two parts of an extractive agent per part of methanol-methyl acetate mixture, recovering essentially pure methanol as overhead product and obtaining the extractive agent and methyl acetate from the stillpot or reboiler, the extractive agent comprises at least a mono nitro hydrocarbon containing from one to eight carbon atoms.

2. The method of claim 1 in which the mono nitro hydrocarbon is nitromethane.

3. The method of claim 1 in which the mono nitro hydrocarbon is nitroethane.

4. The method of claim 1 in which the mono nitro hydrocarbon is 1-nitropropane.

5. The method of claim 1 in which the mono nitro hydrocarbon is 2-nitropropane.

6. The method of claim 1 in which the mono nitro hydrocarbon is nitrobenzene.

7. The method of claim 1 in which the mono nitro hydrocarbon is 2-nitrotoluene.

8. The method of claim 1 in which the mono nitro hydrocarbon is 3-nitrotoluene.

9. The method of claim 1 in which the mono nitro hydrocarbon is 4-nitrotoluene.

10. The method of claim 1 in which the mono nitro hydrocarbon is 2-nitro-m-xylene.

11. The method of claim 1 in which the mono nitro hydrocarbon is 3-nitro-o-xylene.

12. The method of claim 1 in which the mono nitro hydrocarbon is 4-nitro-o-xylene.

13. The method of claim 2 in which the extractive agent comprises a mixture of nitromethane and at least one material from the group consisting of ethylene carbonate, propylene carbonate and ethylene glycol phenyl ether.

14. The method of claim 3 in which the extractive agent comprises a mixture of nitroethane and at least one material from the group consisting of ethylene carbonate, dimethylsulfoxide, ethylene glycol phenyl ether and propylene carbonate.

15. The method of claim 4 in which the extractive agent comprises a mixture of 1-nitropropane and at least one material from the group consisting of ethylene carbonate, propylene carbonate and ethylene glycol phenyl ether.

16. The method of claim 5 in which the extractive agent comprises a mixture of 2-nitropropane and at least one material from the group consisting of ethylene carbonate, propylene carbonate and ethylene glycol phenyl ether.

17. The method of claim 6 in which the extractive agent comprises a mixture of nitrobenzene and at least one material from the group consisting of ethylene carbonate, propylene carbonate and ethylene glycol phenyl ether.

18. The method of claim 7 in which the extractive agent comprises a mixture of 2-nitrotoluene and at least one material from the group consisting of ethylene carbonate, propylene carbonate and ethylene glycol phenyl ether.

19. The method of claim 8 in which the extractive agent comprises a mixture of 3-nitrotoluene and at least one material from the group consisting of ethylene carbonate, propylene carbonate and ethylene glycol phenyl ether.

20. The method of claim 9 in which the extractive agent comprises a mixture of 4-nitrotoluene and at least one material from the group consisting of ethylene carbonate, propylene carbonate and ethylene glycol phenyl ether.

21. The method of claim 10 in which the extractive agent comprises a mixture of 2-nitro-m-xylene and at least one material from the group consisting of ethylene carbonate, propylene carbonate and ethylene glycol phenyl ether.

22. The method of claim 11 in which the extractive agent comprises a mixture of 3-nitro-o-xylene and at least one material from the group consisting of ethylene carbonate, propylene carbonate and ethylene glycol phenyl ether.

23. The method of claim 12 in which the extractive agent comprises a mixture of 4-nitro-o-xylene and at least one material from the group consisting of ethylene carbonate, propylene carbonate and ethylene glycol phenyl ether.

* * * * *